United States Patent [19]
Vining et al.

[11] Patent Number: 5,920,319
[45] Date of Patent: Jul. 6, 1999

[54] AUTOMATIC ANALYSIS IN VIRTUAL ENDOSCOPY

[75] Inventors: David J. Vining; Gordon W. Hunt, both of Winston-Salem; David K. Ahn, Greensboro, all of N.C.; David R. Stelts, Silver Creek, Ga.; Yaorong Ge, Winston-Salem, N.C.; Paul F. Hemler, Winston-Salem, N.C.; Tiffany W. Salido, Winston-Salem, N.C.

[73] Assignee: Wake Forest University, Winston-Salem, N.C.

[21] Appl. No.: 08/805,584

[22] Filed: Feb. 25, 1997

Related U.S. Application Data

[63] Continuation-in-part of application No. 08/331,352, Oct. 27, 1994, Pat. No. 5,782,762.

[51] Int. Cl.⁶ .................................................... G06T 17/00
[52] U.S. Cl. .......................................... 345/420; 345/419
[58] Field of Search ..................................... 345/419, 420, 345/421, 422, 423

[56] References Cited

U.S. PATENT DOCUMENTS

| | | | |
|---|---|---|---|
| 4,367,216 | 1/1983 | Mutzel et al. | 424/5 |
| 4,630,203 | 12/1986 | Szirtes | 364/414 |
| 4,710,876 | 12/1987 | Cline et al. | |
| 4,719,585 | 1/1988 | Cline et al. | |
| 4,729,098 | 3/1988 | Cline et al. | |
| 4,751,643 | 6/1988 | Lorensen et al. | |
| 4,791,567 | 12/1988 | Cline et al. | |
| 4,821,213 | 4/1989 | Cline et al. | |
| 4,831,528 | 5/1989 | Crawford et al. | |
| 4,879,668 | 11/1989 | Cline et al. | 364/522 |

(List continued on next page.)

FOREIGN PATENT DOCUMENTS 9114397  10/1991  WIPO .
9424640  10/1994  WIPO .

OTHER PUBLICATIONS

Vining, D.J., Padhani, A.R., Wood, S., Zerhouni, E.A., Fishman, E.K., and Kuhlman, J.E., "Virtual Bronchoscopy: A New Perspective for Viewing the Tracheobronchial Tree." Radiology. Nov. 1993, vol. 189 (P).

Watt, Alan. "3D Computer Graphics." 2nd Edition, Addison–Wesley Pub. Co., 1993, pp. 320–323.

Strong et al., "Applications of Three–Dimensional Display Techniques in Medical Imaging," J.Biomed. Eng. 1990, vol. 12. May, pp. 233–238.

Oikarinen et al., "Rendering System for Tomographic Images".

Primary Examiner—Phu K. Nguyen
Assistant Examiner—Cliff N. Vo
Attorney, Agent, or Firm—Donald R. Piper, Jr.; Dann, Dorfman, Herrell & Skillman, P.C.

[57] ABSTRACT

A computer system and a computer-implemented method are provided for interactively displaying a three-dimensional rendering of a structure having a lumen and for indicating regions of abnormal wall structure. A three-dimensional volume of data is formed from a series of two-dimensional images representing at least one physical property associated with the three-dimensional structure. An isosurface of a selected region of interest is created by a computer from the volume of data based on a selected value or values of a physical property representing the selected region of interest. A wireframe model of the isosurface is generated by the computer wherein the wireframe model includes a plurality of vertices. The vertices of the wireframe model are then grouped into populations of contiguous vertices having a characteristic indicating abnormal wall structure by the computer. The wireframe model is then rendered by the computer in an interactive three-dimensional display to indicate the populations of abnormal wall structure.

50 Claims, 10 Drawing Sheets

U.S. PATENT DOCUMENTS

| | | | |
|---|---|---|---|
| 4,958,932 | 9/1990 | Kegelman et al. | 365/372 |
| 4,984,157 | 1/1991 | Cline et al. | |
| 4,985,834 | 1/1991 | Cline et al. | 364/413.22 |
| 5,056,020 | 10/1991 | Feldman et al. | 364/413.19 |
| 5,127,037 | 6/1992 | Bynum | 378/4 |
| 5,166,876 | 11/1992 | Cline et al. | |
| 5,170,347 | 12/1992 | Tuy et al. | 364/413.22 |
| 5,187,658 | 2/1993 | Cline et al. | |
| 5,204,625 | 4/1993 | Cline et al. | |
| 5,229,935 | 7/1993 | Yamagishi et al. | 364/413.22 |
| 5,245,538 | 9/1993 | Lis | 364/413.13 |
| 5,261,404 | 11/1993 | Mick et al. | 128/653.1 |
| 5,265,012 | 11/1993 | Amans et al. | 364/413.13 |
| 5,270,926 | 12/1993 | Tam | 364/413.19 |
| 5,283,837 | 2/1994 | Wood | 382/6 |
| 5,295,488 | 3/1994 | Lloyd et al. | 128/653.1 |
| 5,299,288 | 3/1994 | Glassman et al. | 395/80 |
| 5,345,490 | 9/1994 | Finnigan et al. | |
| 5,365,927 | 11/1994 | Roemer et al. | |
| 5,458,111 | 10/1995 | Coin | |

AUTOMATIC ANALYSIS IN VIRTUAL ENDOSCOPY

RELATED APPLICATION

This application is a continuation-in-part of application Ser. No. 08/331,352 now abandoned, entitled "Method and System for Producing Interactive, Three-Dimensional Renderings of Selected Body Organs Having Hollow Lumens to Enable Simulated Movement Through the Lumen", filed on Oct. 27, 1994, now U.S. Pat. No. 5,782,762, which is incorporated herein by reference.

FIELD OF THE INVENTION

The present invention relates to a system and method for interactively displaying a three-dimensional rendering of a structure having a lumen and, more particularly, to a system and method for automatically analyzing such structures for potential abnormalities.

BACKGROUND OF THE INVENTION

For many forms of cancer, early detection is essential for a favorable prognosis. A cancerous growth must be detected at an early stage before the cancer is allowed to grow and spread. This is particularly true for colorectal and lung cancers. As a result, endoscopic techniques have been developed to examine the colon and tracheobronchial airways for the growth of precancerous and cancerous masses.

Regarding colorectal cancer, the American Cancer Society and the National Cancer Institute recommend routine screening beginning at age 55 in order to provide a means for early detection of abnormal growths. Under those guidelines over 50 million Americans should undergo annual colorectal screening. However, only about 1.5 million fiberoptic colonoscopies are performed each year. The discrepancy arises, at least in part, because conventional colonoscopies require a patient to be sedated so that a flexible endoscope can be inserted into the patient's anus. Another problem is that conventional colonoscopies fail to provide access to the entire colon in approximately 15% of cases. Colonoscopies also expose patients to the risk of bowel perforation. Accordingly, it is understandable that patients are reluctant to undergo, or repeatedly subject themselves to, such an invasive procedure.

Consequently, virtual endoscopic techniques have been, and are continuing to be developed. Virtual endoscopy that utilizes computer reformation of radiologic cross-sectional images is a minimally invasive alternative to conventional fiberoptic endoscopy. Virtual endoscopy reduces the risk of perforation, does not require any sedation, and is considerably less expensive than the fiberoptic endoscopy method. For example, virtual colonoscopy techniques generally require bowel cleansing, gas distension of the colon, a 40–60 second spiral computed tomography (CT) scan of a patient's abdomen and pelvis, and human visual analysis of multiplanar two-dimensional (2D) and three-dimensional (3D) images created from CT data.

Although virtual colonoscopy techniques provide excellent images of the colon in three-dimensions, a correct diagnosis hinges upon a physician's ability to properly identify small (approximately 5–10 mm), and sometimes subtle, masses within hundreds of multiplanar two-dimensional and three-dimensional images. Such human inspection is time consuming, tedious, expensive, and under certain circumstances prone to error of interpretation. Accordingly, it would be highly beneficial to provide an automatic virtual endoscopic system and method for automatically analyzing and/or detecting abnormalities, such as abnormal growths, in a targeted structure or organ system, such as the walls of a colon or trachea.

SUMMARY OF THE INVENTION

In accordance with the present invention, a computer-implemented method and computer system are provided for interactively displaying a three-dimensional rendering of a structure having a lumen. In a specific application, the method may be utilized for analyzing regions having certain characteristics of wall structure such as thickness or shape to detect, for example, abnormal masses. In accordance with the method of the present invention, a three-dimensional volume of data is formed from a series of two-dimensional images representing at least one physical property associated with the three-dimensional object. An isosurface of a selected region of interest is created in the computer from the volume of data based on selected values of the physical properties representing the selected region of interest. A wireframe model of the isosurface is generated by the computer. The wireframe model is analyzed to detect, by computer, those sections of the object having the selected characteristic such as abnormal wall structure. For example, the wireframe model includes a plurality of vertices. The computer-implemented method groups the vertices of the wireframe model into populations having a characteristic indicating abnormal wall structure. The wireframe model with highlighted abnormal portions is then rendered by the computer into an interactive three-dimensional display on the computer monitor.

In specific applications, the step of grouping the vertices into populations having a characteristic indicating abnormal wall structure is effected by determining a normal vertex for each vertex position of the wireframe model. Next, a connectivity matrix is determined to provide sets of contiguous vertices for each vertex. A wall thickness value associated with each normal vector is determined for each vertex. Local convexity and curvature are also determined on a per vertex basis. Then, contiguous vertices having a characteristic indicating abnormal thicknesses or other abnormal properties are grouped together into separate populations indicative of areas of abnormality. Either as a supplement or an alternative to determining abnormal thicknesses, the computer-implemented method may function to analyze shape characteristics of selected populations of vertices. For example, each population of contiguous vertices may be determined based on a characteristic such as convexity or curvature. Each population is then analyzed to determine a convexity value for each population representing an amount and direction of convexity of the population on the wireframe model. In selected applications, each population may be analyzed according to other selected shape characteristics.

In accordance with the present invention, a method and system are provided for interactively displaying a three-dimensional rendering of a structure having a lumen wherein the rendering is effected by a an adaptive thresholding procedure. A three-dimensional volume of data is formed in a computer from a series of two-dimensional images acquired, for example, by a scanner such as CT-scanner. The acquired images represent at least one physical property associated with the three-dimensional object. A selected region of interest is segmented by the computer from the volume of data based on a selected criteria such as a threshold value of the physical property. The threshold value is adaptively adjusted in the region of interest to control the segmenting of the selected region of interest. An isosurface of a selected region of interest is created by the computer from the volume of data based on selected values, such as the adaptive adjusted thresholds of the physical property representing the selected region of interest. Next, a wireframe model of the isosurface is generated and then rendered in an interactive three-dimensional display.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

The present invention generally relates to a method and system, as schematically represented in FIGS. 1–4, for generating interactive, three-dimensional renderings of three-dimensional structures generally having a lumen. The structures are usually in the general form of selected regions of a body and in particular, human or animal body organs which have hollow lumens such as colons, blood vessels, and airways. In accordance with the present invention, the interactive three-dimensional renderings are generated in a computer-controlled process from a series of two-dimensional, cross-sectional images of the selected body organ acquired, for example, from a helical (computed tomography (CT) Scan. The three-dimensional renderings are interactive in that such renderings can be manipulated by a user on a visual display of a computer system, such as a computer monitor, to enable movement in, around and through the three-dimensional structure while simultaneously displaying multiplanar views centered on a point that changes in response to the movement, or on a point selected by the user.

The computer-generated interactive three-dimensional renderings can be constructed from surface renderings of the organ system or from volume renderings of the organ system and surrounding anatomy and, often, presented simultaneously in the same three-dimensional display window. In a selected embodiment, a surface rendering of an organ can be incorporated into a volume rendering of the surrounding anatomy using texture memory in order to achieve a combined surface/volume rendering, or a hybrid rendering effect, wherein the surface rendered organ may be highlighted in the context of the volume-rendered surrounding anatomy. In yet another embodiment, multiplanar views such as orthogonal (sagittal, coronal, and axial) or oblique views, may be presented simultaneously with a surface-rendered organ and surrounding volume-rendered anatomy in either separate three-dimensional display windows or in a combined single three-dimensional or display window.

Figure 4:
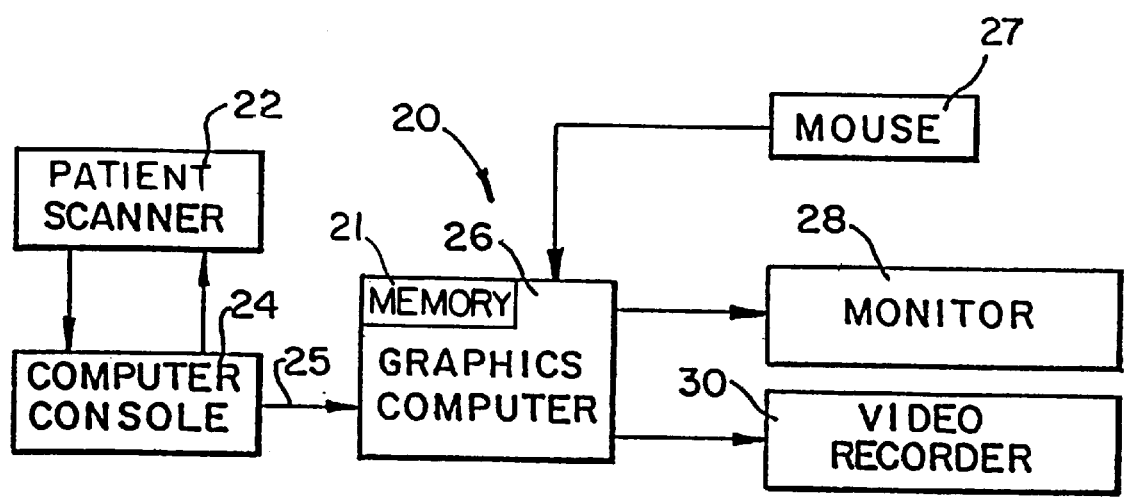
FIG. 4 is a block diagram of a system used in the method of the present invention.

A computer-controlled system 20 in accordance with the present invention is shown schematically in FIG. 4. The system 20 is generally as described in co-pending application Ser. No. 08/331,352, which is incorporated herein by reference. Briefly, a computer console 24 is used to operate a scanner 22 to produce a series of two-dimensional, cross-sectional images of a selected three-dimensional object. The two-dimensional images are transferred from the console 24 to a computer graphics workstation 26 over a computer network 25. The graphics computer 26 is used to generate a three-dimensional rendering, such as a three dimensional surface rendering, of the selected object and to automatically identify potentially abnormal regions of the structure. The three-dimensional rendering is displayed on a computer monitor 28. Additionally, the displayed rendering can be recorded on a video recorder 30 or photographed for future viewing. Various inputs, such as a computer mouse 27, are provided to the graphics computer to permit a user to manipulate the displayed imagery.

The scanner 22 can be a General Electric HiSpeed Advantage Helical CT Scanner (GE Medical Systems, Milwaukee, Wis.). For scanning a patient's lungs, the scanner is typically operated with an X-ray beam collimation of 3 mm, a pitch of 1:1, a 1 mm reconstruction interval, a display field-of-view of 25.6 cm, and a 512×512 matrix. For scanning a patient's colon, the scanner is typically operated with a beam collimation of 5 mm, a pitch of 2:1, a 1 mm reconstruction interval, a display field-of-view of 40 cm, and a 512×512 matrix. These protocols typically result in approximately 200 thoracic CT images or 500 abdominal CT images, which occupy approximately 100 MB and 250 MB of disk storage space, respectively. However, the protocols can be modified to optimally acquire image data of specific organ systems.

The image data can be stored in any of a variety of image formats. For example, the image data can be stored in the digital imaging and communications in medicine (DICOM) standard, or as raw binary slices, or in a variety of volume formats. For example, the image data can be stored in the computer memory in an internal data format which allows the image files to be saved as a single data volume instead of individual image files. The internal data format can also permit standard compression and uncompression techniques to be incorporated, thereby reducing computer disk storage requirements.

Figure 1:
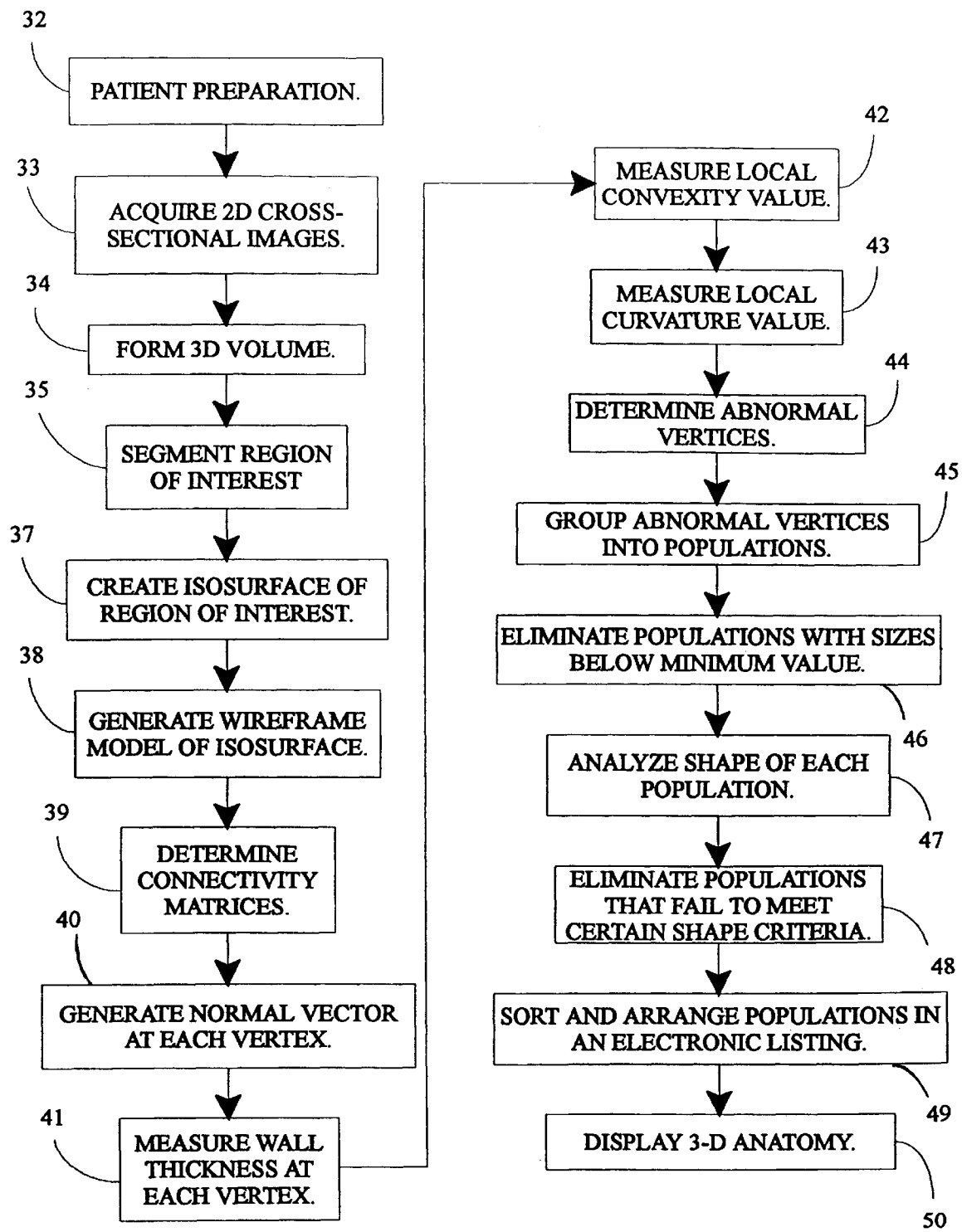
FIG. 1 is a flowchart representing a method in accordance with the present invention of producing an interactive, three-dimensional rendering of a selected organ system, such as a lumenous organ, and of detecting potentially abnormal areas of the organ system.

A method for generating interactive, three-dimensional renderings of a selected structure having a lumen and indicating potentially abnormal regions of the structure in accordance with the present invention is generally set forth in FIG. 1. The method can be implemented by computer. The steps of patient preparation 32, acquisition of two-dimensional images 33, formation of a three-dimensional volume 34, segmentation of a region of interest 35, creation of an isosurface of the region of interest 37, and generation of a wireframe model of the isosurface 38 may be effected in the general manner described in co-pending application Ser. No. 08/331,352, which is incorporated herein by reference or any comparable methodologies and algorithms.

Patient preparation 32 will be dictated by the organ system to be rendered. For example, if the patient's colon is to be rendered, the patient is prepared using bowel cleansing and insufflation with gas to distend the colon. In addition, the patient can be given an oral contrast agent to become incorporated in the fecal content to readily distinguish the stool from surrounding soft tissue structures, including the colon wall. Without adequate bowel cleansing or use of an oral contrast agent, stool and normal colon wall or colon lesions can be indistinguishable in computed tomography or other radiologic modality images. For example, the contrast agent may comprise a low-density (e.g., 1.5% w/v) barium-containing mixture. The opacified stool may then be digitally substracted from the CT image data in order to render an unimpeded colon. Alternatively, for rendering a patient's airways, the patient can be administered a bolus of non-ionic intravenous iodinated contrast agent to aid in distinguishing the blood vessels surrounding the airways.

Once the patient has been prepared, two dimensional, cross-sectional images of the selected structure are acquired at step 33 with the use of a scanner 22, such as a helical computed tomography (CT) scanner or magnetic resonance imaging (MRI) scanner. The two-dimensional images are arranged in computer memory 21 (i.e., random access memory (RAM)) to create a three-dimensional data volume at step 34. To create isocubic volume elements (i.e., voxels), an interpolation method, including but not limited to trilinear interpolation, can be applied.

At step 35, a region of interest is segmented from the three-dimensional data volume. The purpose of segmentation is to isolate a region of interest within the three-dimensional data volume prior to three-dimensional rendering. In general, medical image segmentation is complicated by image noise, partial volume effects, and the fact that similar intensity values are shared by different anatomical structures. However, when a thin-walled soft tissue structure encompasses an air-filled lumen, segmentation of that structure can be effectuated by selecting the air column as the region of interest. The air column can be effectively segmented because the boundary between air and soft tissue is relatively distinct and sharp. Further, the outside surface of the air column corresponds to the inside surface of the organ of interest. Similarly, when a thin-walled soft tissue structure encompasses a contrast enhanced blood-filled lumen, segmentation of that structure can be effectuated by selecting the contrast-enhanced blood column as the region of interest. Accordingly, a simple thresholding or region growing technique, along with a morphological dilation away from air or blood vessel and towards soft tissue, can be utilized for segmentation purposes.

However, in order to refine and to improve the accuracy of the segmentation process, especially as selected structures have varying characteristics (e.g., changing diameter, wall thickness, and/or X-ray attenuation values), more sophisticated segmentation procedures can be employed. One such procedure adaptively adjusts the threshold value defining the region of interest to more accurately segment specific sections of the organ during a region growing process. For example, adaptive thresholding techniques can be used to segment a patient's airways, especially as a threshold value of −425 Hounsfield units (HU) may be appropriate for the larger airways, but −800 HU may be more appropriate for smaller airways. Therefore, by varying the threshold value between these two extremes, the influence of airway structure and surrounding tissues can be accounted for, especially as partial volume effects become apparent in the smaller airways.

Figure 6:
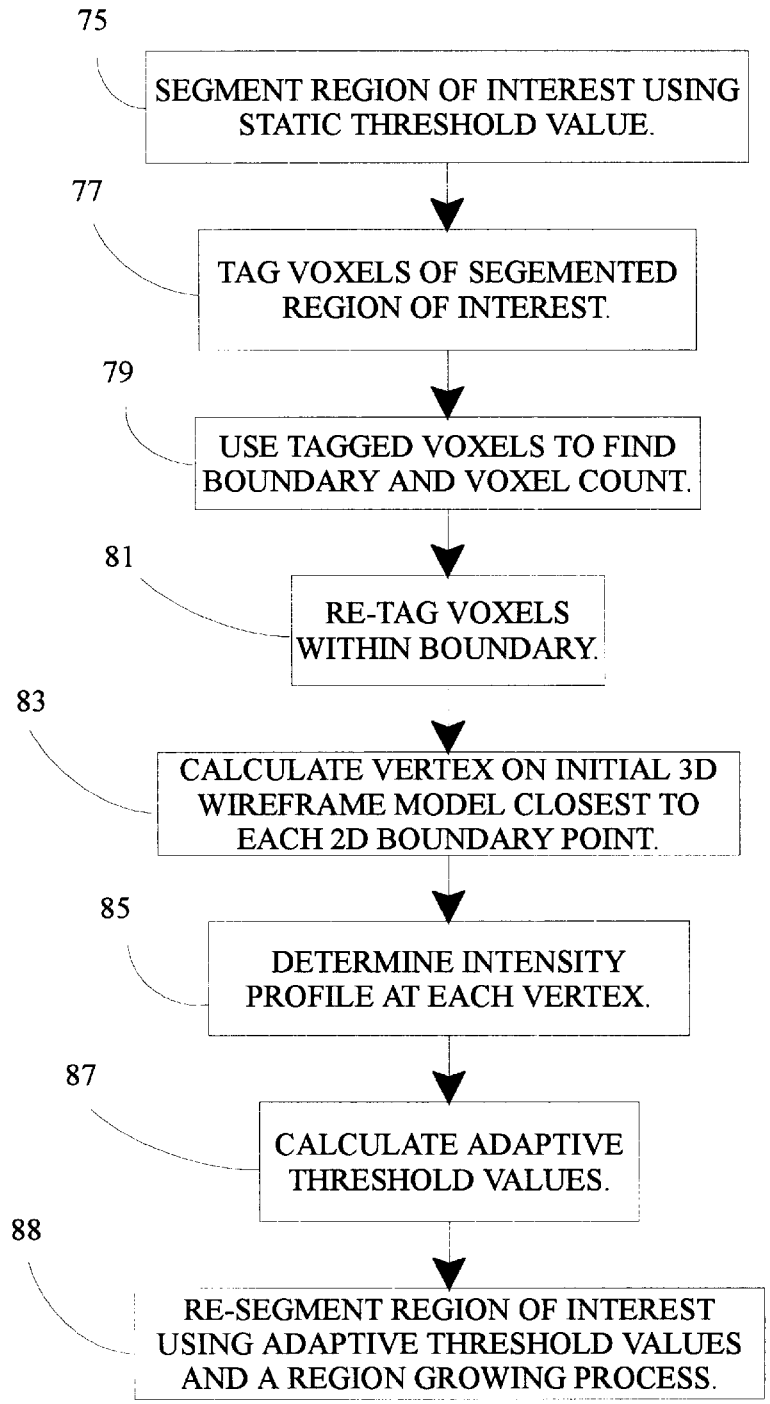
FIG. 6 is a flowchart representing a method for adaptively adjusting a threshold value during the segmentation of a region of interest.

A computer-executed method for adaptively adjusting threshold values for the airways is shown in FIG. 6. At step 75, the region of interest is segmented using a three-dimensional region growing technique and an initial static threshold value. The threshold value chosen should approach the maximum threshold value which can be selected without having the segmentation procedure fail by including surrounding structures as part of the region of interest. For example, when segmenting the air column of an airway, an initial threshold value of −800 HU may be appropriate. An initial wireframe model of the anatomy is created using a marching cubes variant.

The voxels or volume elements of the segmented region of interest are tagged at step 77 by setting a high-order bit in the 16-bit computer word used to store the voxel values (usually only the lower-order 12 bits of a 16 bit word hold any actual data). At step 79, the tagged voxels are used to find the boundary and voxel counts in two-dimensions for each airway segment on every image slice. The voxels within each boundary are distinctly re-tagged at step 81 by setting a different high-order bit. At step 83, the vertices on the initial three-dimensional wireframe model closest to each two-dimensional boundary point of each segment are found. An intensity profile along each vertex's normal vector is calculated to measure x-ray attenuations factors incremental along the normal directions at step 85. The intensity profiles extend bidirectionally, into the surrounding tissue until the voxel values begin to decrease, and into the airway lumen until the voxel values begin to increase.

The adaptive threshold value is calculated for each segment on every image at step 87 as an average value of several measured threshold values for each segment. Each adaptive threshold value can be calculated as a variable percentage of the difference between the average maximum and minimum attenuation factors for the corresponding intensity profile. For example, a percentage of 50% corresponds to the full-width-at-half-maximum measure of the intensity profile. The adaptive threshold values are then used to re-segment the region of interest at step 88 using a region growing process that can account for the varying threshold values.

Alternatively, the adaptive threshold values can be calculated by morphing a ring which represents the intersection of the airway and a perpendicular plane along the skeleton of the airway. The skeleton is a sequence of connected points that lie along the center of the air columns, like a central path. The initial reference ring lies in the initial perpendicular plane and is the set of iso-value points of an underestimated threshold value on that plane in the largest branch of the airway. Using this ring as a reference, the threshold value is changed to create a new ring in the same plane, with a larger circumference and larger curvature values than the reference ring. If the increase in circumference and curvature values are below a certain limit, then the old threshold value is replaced by the new threshold, and the process is repeated. When the maximums are exceeded, the new threshold value is stored on the skeleton, the perpendicular plane is shifted to the next point on the skeleton, and the previous threshold value is used as the initial threshold value for the iso-value ring on the new plane. This process is repeated for every branch along the skeleton until every point in the skeleton has an associated adaptive threshold value. A variant of the marching cubes can then be used to generate a variable-value surface using the variable threshold values.

Another method for adaptively adjusting the threshold valve used to grow an object, uses the morphological skeleton of an approximate object to choose optimal threshold values for all parts of the final object. The object is first grown using a lower threshold value. This gives the base structure, but usually does not accurately segment all of the object. Then, the medial axis is calculated from the morphological skeleton of the object. For each voxel on the medial axis, the algorithm searches out (in bi-directional rays perpendicular to the local axis) the local maxima and minima of voxel values along the search line. The full-width-at-half-the-maximum value, or a variable percentage value, is then calculated for each bi-directional ray, and all rays for a particular axis point are averaged to give a threshold value at the axis point. During segmentation, the nearest axis point to the current voxel is determined, and the threshold value associated with that point is used to classify the voxel as being inside or outside the object using a region growing procedure.

Yet another technique for adaptive thresholding involves manually specifying markers in the volume to hold threshold values that best approximate the object at that location. The markers are established for all sections of the object that need special threshold values. A global threshold value is also specified. During the region growing segmentation process, the algorithm checks to see if the current voxel is near a threshold marker. If so, the threshold value associated with the marker is used to classify the voxel as being inside or outside the object. The range for calling a position near the marker, as well as the behavior if the position is inside the specified range (the threshold can be linearly scaled or applied unchanged), can be user-specified. However, if the current voxel is not near a threshold marker, the global threshold is used to classify the voxel.

Still another technique for adaptive thresholding modifies the threshold value as a function of the distance from the starting seed of the region growing procedure. The user may specify that voxels near the seed should be within a certain range, but voxels farther away from the seed should fall within a different range. The thresholds for positions in between can be found by interpolating between the ranges. For this technique, any number of distance and threshold ranges can be specified.

Returning to FIG. 1, once the region of interest has been segmented, an isosurface of the region of interest is created at step 37. The isosurface can be generated using a variant of a marching cube algorithm. The isosurface is then used to generate a wireframe model at step 38. The wireframe model comprises a polygonal mesh that corresponds to the surface of the region of interest.

After the wireframe model has been generated at step 38, connectivity matrices are determined at step 39. The connectivity matrices are data structures which provide information regarding the connectivity between the vertices and polygons which comprise the wireframe model. The connectivity matrices are determined by traversing the polygon and vertex lists associated with the wireframe model, generating sets of immediate neighbor vertices and triangles associated with each vertex and polygon in the lists. For example, the vertex to polygon connectivity matrix contains, for each vertex in the wireframe model, a list of all polygons that contain that vertex. Likewise, a polygon to polygon matrix lists all adjacent polygons for each polygon in the model.

Using these connectivity matrices, the polygon list of the wireframe model is then re-ordered. The polygons generated using the variant of marching cubes are usually added to, and as such ordered in, the polygon list as the three dimensional volume is traversed. Accordingly, all of the polygons between the first and second images are generated first, followed by the polygons between the second and third images, and so forth. This polygon ordering is not intuitive, nor ideal for analysis or manipulation of the geometry at the local connectivity level. Consequently, to group vertices into populations and to analyze the populations, it is advantageous to re-order the polygons into the sequence by which they would be encountered while "traveling" through the lumen of the wireframe model. In addition, the re-ordering facilitates rapid three-dimensional renderings, since hidden objects or objects outside of the field-of-view can be easily identified and removed, thereby reducing the number of polygons rendered and thus increasing the rendering speed.

The re-ordered connectivity matrices are also a means to rapidly calculate an arbitrarily oriented cross-sectional area of an object or a region of interest. This is done by generating the intersection of the wireframe model with a plane of user-defined orientation. Three user-defined points of intersection with the object defines the plane. The intersection of the plane with the wireframe model is outlined by a set of points that are generally in the shape of a distorted ring. By connecting these N points, a polygon with N sides is formed. This polygon can be divided into N-2 triangles by connecting the first point in the ring with every other point on the ring. The cross-sectional area can be approximated by summing the areas of each triangle.

The vertices of the wireframe model can be analyzed and grouped into populations having abnormal wall structure as shown at steps 40–45 in FIG. 1. At step 40, a normal vector is calculated for each vertex in a the wireframe model. The direction of each normal vector is perpendicular to a plane that is tangent to the isosurface at each such vertex, typically pointing away from the object or away from the lumen of a body organ. The normal vectors at the respective vertices can be computed as the average of the normal vectors associated with each polygon connected to that vertex. The normal vector associated with a polygon is calculated using a vector cross product. Alternatively, the normal vector at a vertex can be computed as a weighted average of the normal vectors associated with those polygons of the wireframe model which are within a predetermined distance from a specific vertex. A third method is to compute the normal vector at a vertex, component-wise (e.g., x, y, and z), by calculating the three dimensional gradients of the local volume surrounding the vertex.

The wall thickness of the structure at each vertex is measured at step 41. The wall thickness at a given vertex can be determined by measuring the distance from the inner surface of the selected object to its outer surface or some other position between the inner and outer surfaces. For body parts such as the colon or airways, the selected structure's wall is composed of soft tissue and the lumen of the structure comprises air. Accordingly, the inner surface corresponds to an air/soft tissue interface. Further, the colon and airways are typically surrounded by fat, air, or other non-soft tissue material (i.e., contrast-enhanced blood vessels, bone, or calcification). Accordingly, the outer surface corresponds to the soft tissue/air, soft tissue/bone, soft tissue/fat, or other such interface. The X-ray attenuation factors for air (approximately −1024 HU to −425 HU), fat (about −200 HU to −20 HU), and other non-soft tissue structures such as contrast-enhanced blood vessels and bone (approximately >100 HU) are distinct from the soft tissue component (about 20 HU to 100 HU) of the airways or colon wall. Accordingly, the wall thickness at a vertex on the wireframe model can be calculated from the volume data of the selected organ, which can be measured at regularly spaced intervals along each normal vector, as will now be described.

In general, for each vertex, v, and its corresponding normal vector, N, an X-ray attenuation factor, A(pi), can be determined for each point pi along the normal, where $p_i = v + iN$ for $1 \leq i \leq$ max_depth and max_depth is a user-definable maximum search depth, typically set at 15. The wall thickness value, T, is initially set to zero but is incremented by one for each consecutive point pi which has a corresponding X-ray attenuation value that falls within a range of −425 HU to +100 HU and that satisfies certain criteria.

Figure 3:
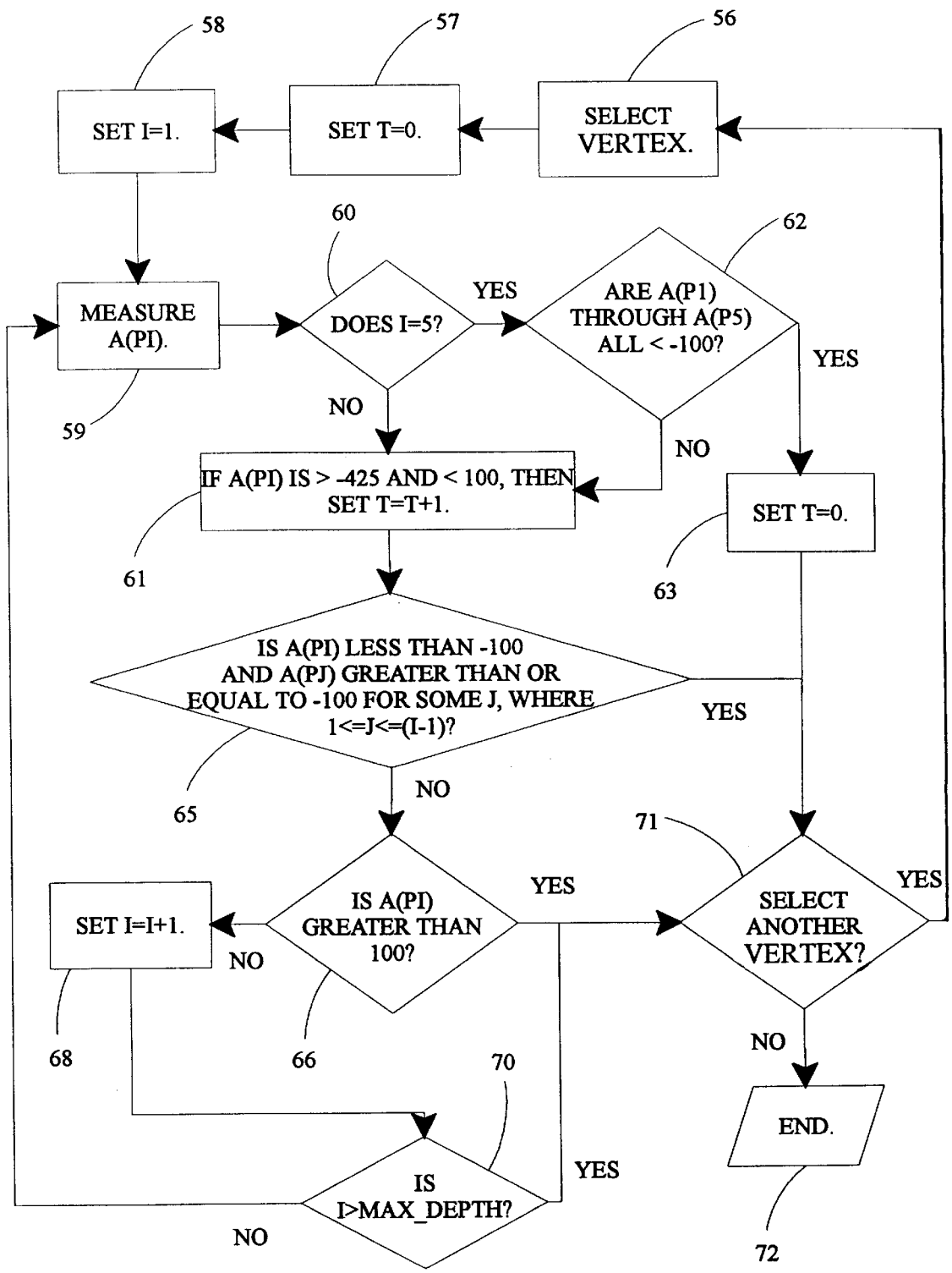
FIG. 3 is a flowchart representing a method for measuring the selected organ system's wall thickness.

Specifically, the wall thickness at each vertex can be measured as shown in FIG. 3. At step 56, one of the vertices, v, of the wireframe model is selected. The thickness, T, at that vertex is initially set to zero at step 57 and a counter, i, is set to one at step 58.

The voxel value, such as the x-ray attenuation factor, $A(p_i)$, for the $i^{th}$ point along the normal is measured at step 59. At step 60, it is determined whether i=5. If i does not equal 5, then it is determined if $A(p_i)$ is between −425 HU and +100 HU, and if $A(p_i)$ is between −425 HU and +100 HU, then the thickness T is incremented by one at step 61. The process proceeds to step 65.

At step 65, it is determined whether $A(p_i) < -100$ HU and $A(p_j) \geq -100$ HU for some value of $1 \leq j \leq (i-1)$. If this expression is satisfied, then a soft tissue/fat or soft tissue/air interface is considered to have been reached. Accordingly, the thickness T is not incremented and the process proceeds to step 71.

At step 71, it is determined whether there is a vertex whose thickness has not yet been measured. If there is a vertex whose thickness has not been measured, that vertex is selected at step 56. Otherwise, the wall thickness at all vertices would have been measured and the process ends at step 72.

Returning to step 65, if the expression at step 65 is not satisfied, then it is determined at step 66 whether $A(p_i) > 100$ HU. If $A(p_i)$ is greater than 100 HU, then a soft tissue/bone interface or an interface with some other high-density material is considered to have been reached. Accordingly, the thickness T is not incremented and the process proceeds to step 71.

If $A(p_i)$ is not greater than 100 HU at step 66, then the process proceeds to step 68 where counter i is incremented by one. At step 70, it is determined if counter i exceeds the predetermined value of max_depth. If i>max_depth, then the process proceeds to step 71. If, however, i≦max_depth, then $A(p_i)$ is measured at step 59.

Returning to step 60, if i=5, then the attenuation factors for the first five points, $A(p_1)$ through $A(p_5)$, are evaluated at step 62 to determine if all of those attenuation factors are less than −110 HU. If all of those attenuation factors are less than −110 HU, the wall thickness at that vertex is considered to be normal. This situation often arises along the colon's haustra, or where opposing segments of gas distended bowel touch. Accordingly, the thickness value, T, is set to zero at step 63 and the process proceeds to step 71. By assigning T=0 to a vertex, v, that vertex is considered to be associated with normal colon wall.

Returning to step 62, if the attenuation value at any of the first five points ($A(p_1)$ through $A(p_1)$) exceeds −110 HU, then the wall thickness determination continues at step 61.

Since the wall thickness of body structures such as the colon may be inadvertently or artificially increased, such as during musculature contraction of the colon at certain positions along the colon structure, many of the regions of abnormal thickness may not be indicative of true lesions. Instead, the thickened regions may represent normal structural elements, such as regions where the colon is contracted or where it touches solid organs. Accordingly, it can be beneficial to further analyze and characterize each vertex associated with abnormal thickness to refine the list of potentially abnormal vertices. Additional local shape features can be used to characterize and associate vertices as being abnormal.

For example, a local convexity value at each of the surface vertices can be determined at step 42. The local convexity values can be determined for all vertices, or for only those vertices associated with abnormal wall thickness. For each vertex, its neighboring vertices within a connected neighborhood of a pre-determined size (e.g., 3), is determined using the connectivity matrices. A local convexity value for each vertex, v, is computed as:

$$C = \sum_{i=1}^{n} D(v_i)$$

wherein $D(v_i)$ is the distance from the $i^{th}$ neighboring vertex to a plane through v and perpendicular to v's normal vector, and n is the number of neighboring vertices. Vertices associated with a convexity value of greater than a pre-defined maximum (e.g., >2) can be considered abnormal.

In addition, the local curvature at each vertex in a population can be determined at step 43 in FIG. 1. The curvature reflects another shape feature of the object's surface at a given vertex. Vertices associated with broad curvatures indicate regions that are relatively flat. Accordingly, if the user wishes to identify only regions having thicknesses that vary significantly over short distances, those vertices with small curvatures may be labeled as abnormal.

The local curvature at each vertex in a population can be determined by summing the scalar distance between each of a user-determined number of levels, N, of adjacent vertices and the plane perpendicular to the normal of the vertex. The result is then normalized by the surface area outlined by the $N^{th}$ level of adjacent vertices. Because the direction of the curvature is ignored, the technique is able to detect areas of small curvature.

At step 44, vertices representing an abnormality are selected. Those vertices meeting selected criteria can be identified as abnormal vertices. For example, vertices having abnormal thickness and/or convexity and/or curvature criteria may be identified as abnormal vertices. In a specific application, the wall thickness values, local convexity values, and local curvature values can be used, independently or in conjunction with each other, to either accept or reject vertices as being abnormal. The individual parameters can be combined using a logical AND operation.

At step 45, the vertices on the wireframe model associated with abnormal structure (i.e., having a combination of associated abnormal wall thickness and/or abnormal shape, such as abnormal local convexity and/or abnormal local curvature) are grouped into populations. The re-ordered connectivity matrices are used to determine if vertices associated with abnormal parameters are directly connected to other vertices that are also associated with abnormal parameters. Accordingly, each formed population represents a potential abnormal lesion. In addition, each population can be further analyzed and characterized by its size, dimensions, or other statistical quantities.

Generally, the size of a population is indicated by the number of vertices which comprise the population. At step 46, those populations having a size below a predetermined minimal value are excluded from being considered abnormal. If the size of a population is sufficiently small, then the population is unlikely to represent a true lesion. Instead, the population more likely represents a normal aberration in the structure or image segmentation process. Accordingly, elimination of those populations having a size below a minimum value, decreases the occurrence of false positive findings.

Each population is further analyzed according to shape at step 47 to reduce the occurrence of false positive findings. Since the structure of body organs may appear abnormal, either inadvertently or artificially, such as during muscular contraction of the colon at certain positions along the colon's structure, many of the abnormal populations may not be indicative of true lesions. Instead, these populations may represent normal structural elements, such as regions where the colon is contracted or where it touches solid organs. Accordingly, it may be advantageous to further analyze and characterize each population identified as having an abnormal structure to further refine the list of potential lesions and to increase the likelihood that a detected population represents a true abnormality.

Figure 2:
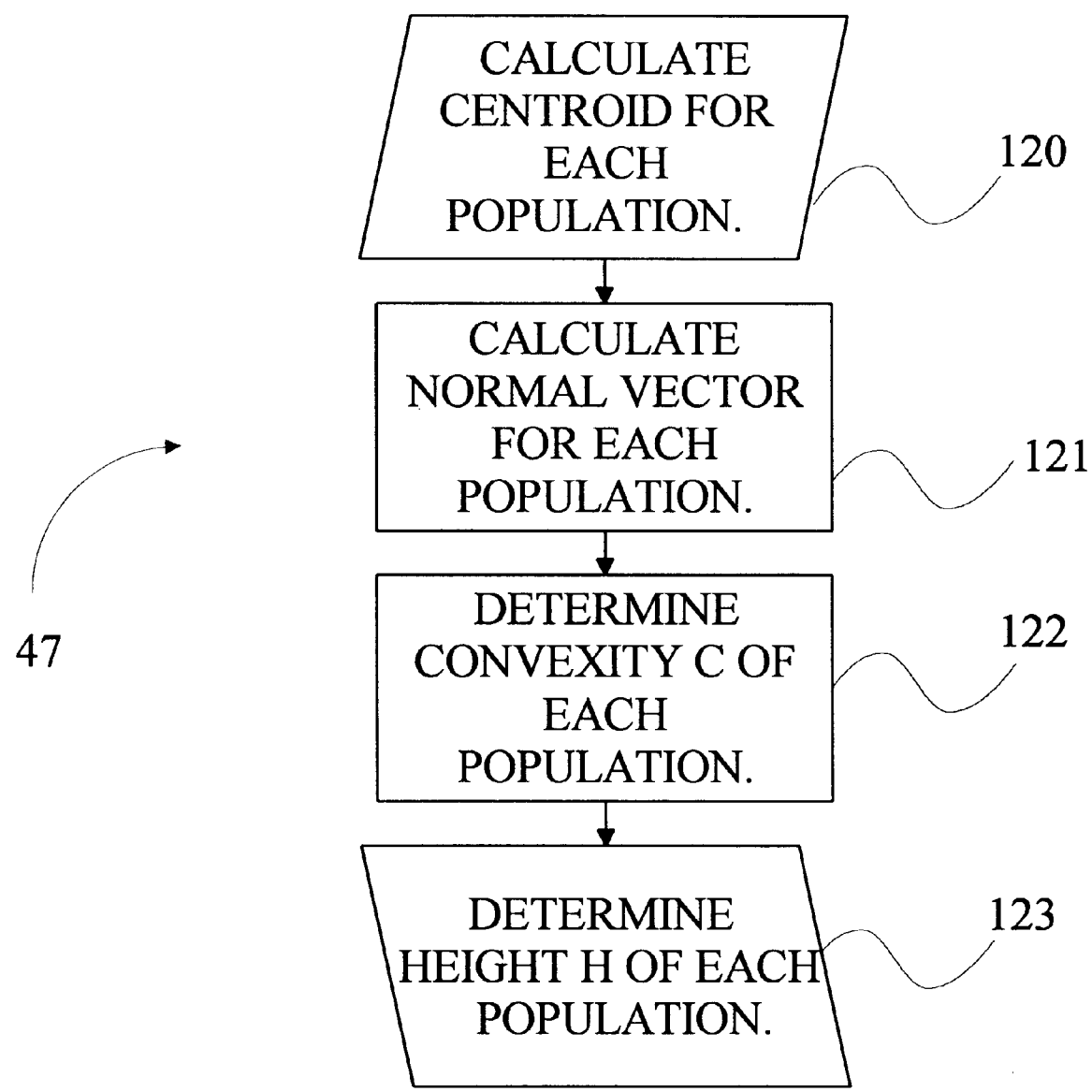
FIG. 2 is a flowchart representing a method for analyzing the shape of a population representing a potentially abnormal area within the selected organ system.

For example, the shapes of the populations can be analyzed, characterized, and accepted or rejected as being abnormal as illustrated in detail in FIG. 2. At step 120 a centroid for each population is calculated. The centroid can be computed as a weighted sum of the positions of each vertex within the population. The individual vertices can be weighted by their associated wall thickness values or other parameters. Once the centroid has been determined for a population, the height and normal vector for that population can be determined.

A population normal vector is calculated for each population at step 121. The population normal vector can be computed as a sum of the normal vectors at each of the vertices within the population, and the individual vertex normal vectors can be weighted by their corresponding wall thickness values or other parameters.

Figure 5:
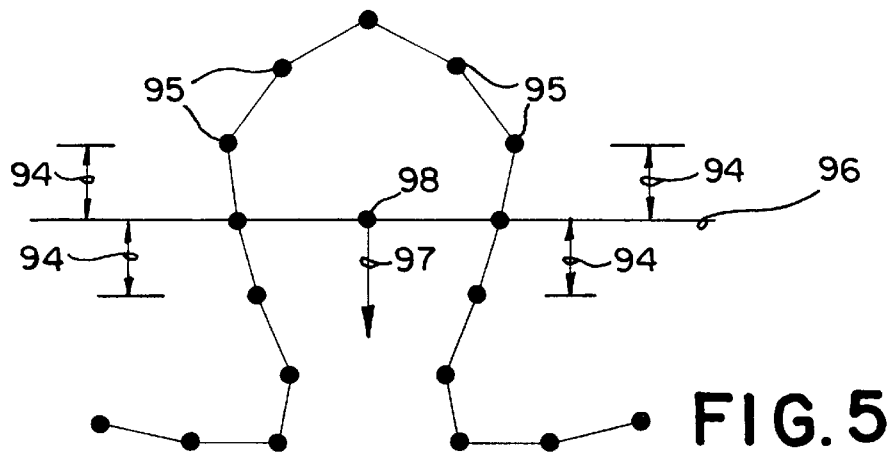
FIG. 5 is a schematic representation of a two-dimensional plane through a wireframe model of an area of abnormal wall structure illustrating a method for determining the convexity of the area.

The convexity value, (C), for each population is determined at step 122. The convexity is a measure of the direction and magnitude of the shape of the surface of the population. As shown in FIG. 5, the convexity of a population is computed as the sum of the distances 94 from vertices 95 in the population to a plane 96, perpendicular to the population normal vector 97 passing through the centroid 98, according to the equation:

$$C = \sum_{i=1}^{n} D(v_i)$$

wherein $D(v_i)$ is the distance from the $i^{th}$ vertex of the population to the plane 96 and n is the number of vertices 95 within a predetermined space relative to the centroid. Since the normals at each vertex are typically assigned to point away from the center of the object, or the lumen of the object, a population which protrudes into the lumen of the object would have a positive convexity value, whereas a population that projects away from the lumen would exhibit a negative convexity value. When the structure is a colon, populations with a negative convexity value are excluded from being considered abnormal, since abnormal colon masses tend to project into the lumen of the colon and would have a positive convexity value.

Further, the higher the magnitude of the convexity value, the greater the slope of the surface of the population. When the structure is a colon, only populations having a positive convexity value above a minimum value are reasonably expected to be potential lesions, since cancerous colon masses are generally manifested by steeply sloped growths that protrude into the lumen of the colon.

The height (H) of each population is determined at step 123. The height is calculated as the difference between the distance of the vertex farthest from a plane 96, perpendicular to the population normal 97 and passing through the centroid 98, and the distance of the vertex closest to that plane according to the equation:

$$H = \text{MAX } D(v_i) - \text{MIN } D(v_i).$$

The height provides an indication as to whether a population is reasonably expected to be a true lesion since populations with large heights are more likely to represent abnormal masses.

Other shape features may be used to include or exclude populations in the list of potential lesions. For example, if a population has a long axis dimension that is greater than a multiple (e.g., 10 times) of the short axis dimension, and the short axis dimension is, for example, less than 5 mm wide, then the population might be considered to be normal. Accordingly, the shape features discussed herein are included only by way of example, and are not intended to limit the scope of the invention.

Referring again to FIG. 1, after the populations with abnormal wall structure (i.e., wall thickness, convexity, or other shape feature) have been identified and characterized, populations that fail to meet certain criteria are eliminated as potential lesions at step 48.

At step 49, those populations which are still considered to represent potential lesions are sorted and arranged in an electronic listing. The listing could be sorted according to such properties as size, convexity, curvature, height, mean wall thickness, standard deviation of wall thickness, other statistical quantities, or a combination of such parameters (e.g., the product of the group convexity value, C, and the group height value, H). Each population in the listing could be linked to a three-dimensional camera position that best illustrates it in the three-dimensional display. Accordingly, the user could choose a population from the listing and thereby be presented with a view of the abnormal area as it appears in the three-dimensional rendering. One means of linking the population to a three-dimensional rendering camera position is by providing the user with a three-dimensional camera view of the population that is parallel to the population normal and centered on the centroid of the population, and set at a chosen distance from the centroid. In one embodiment, the user is presented with two views of the selected population, one from an external perspective and the other from an internal perspective (i.e., from within the lumen of the structure).

A three-dimensional rendering of the wireframe model is displayed at step 50. In one embodiment, the user can navigate through a three-dimensional rendering of the wireframe model which is displayed on the monitor 28. The detected abnormal populations are displayed with a contrasting color scheme to distinguish them from the remainder of the rendered structure, so that the abnormal populations can be quickly and easily identified by human visual inspection. Further, the color scheme can reflect variations in wall thickness, convexity, or curvature, or some other parameter. For example, the normal portions of the rendered structure can be displayed in shades of pink while the potentially abnormal populations are displayed in shades of blue. More specifically, vertices could be assigned colors ranging from dark blue (for vertices with minimum abnormal thickness) to bright blue (for vertices with maximum abnormal wall thickness) to provide a stark contrast to the pinkish color assigned to the normal portions of the rendered structure.

Instead of navigating through the rendered structure, a "split open" view of the three-dimensional rendered structure can be displayed, thereby allowing the user to view the interior surface of the structure, like a topological map, without visual obstruction. The splitting can be accomplished using the re-ordered connectivity matrices, described above, and a central path to divide the wireframe model into several smaller segments, and then split each segment in half to expose the interior surfaces of the segments. The use of the connectivity matrices allows for the splitting of the wireframe to be independent of the degree of overall curvature of the central path of the wireframe model. This approach overcomes the mathematical restrictions inherent in other commonly used cutting plane techniques, such as found in a single infinite cutting plane, spherical-shaped cutting plane, or cylindrically-shaped cutting plane, and allows for an arbitrary number of segments to be split with only a single pass over the wireframe's polygon listing.

Figure 8:
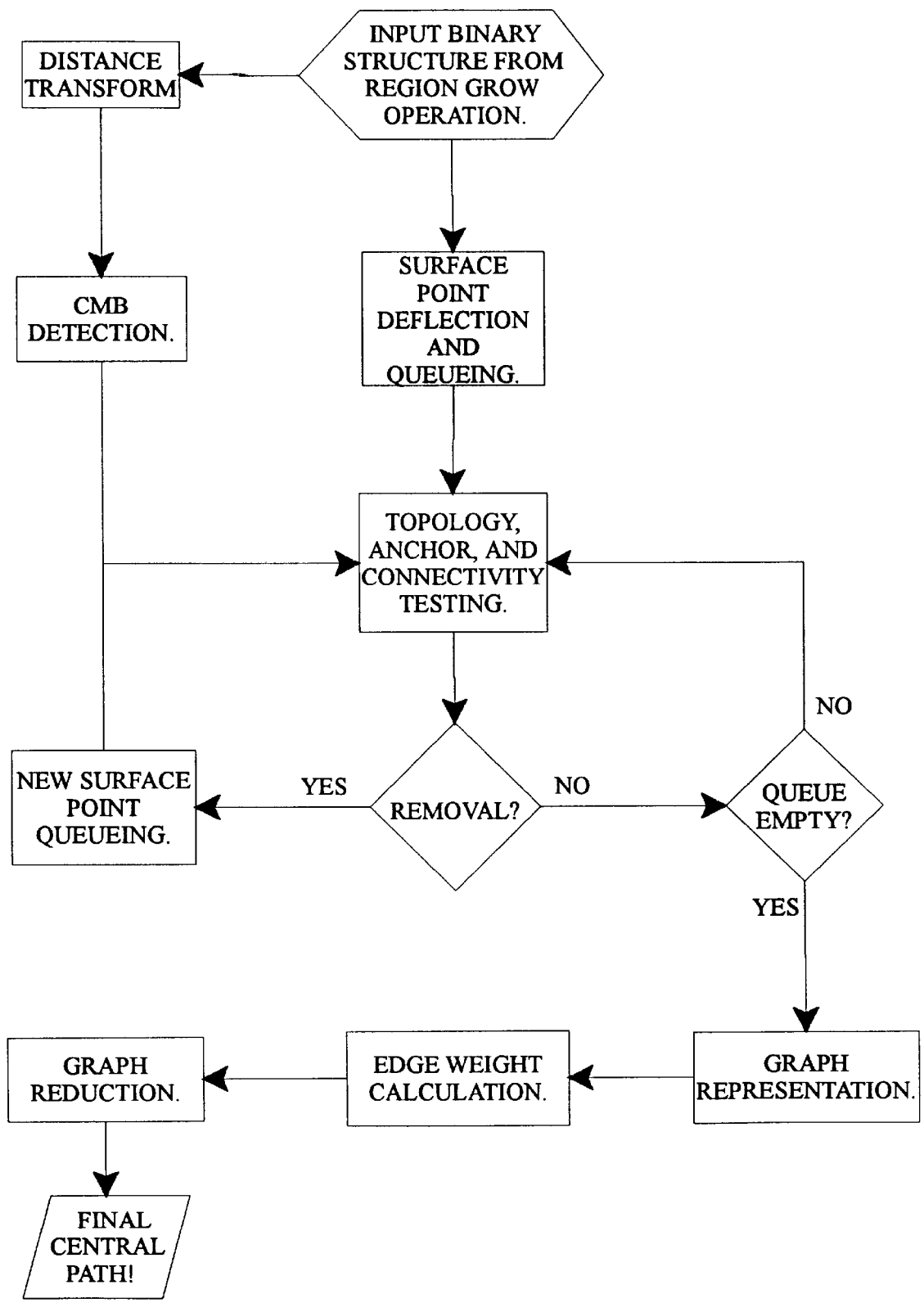
FIG. 8 is flowchart representing a method for determining a central path through the lumen of a hollow organ.

The splitting is accomplished by first approximating a curved cutting surface with a sequence of finite, intersecting planes. These planes contain (i.e., pass through) the central path of the wireframe model. The central path can be calculated, as shown in FIG. 8, by first generating points that are medially located within the colon or lumen. Second, the detected medial points are linked into connected central paths and the path that is most appropriate for colon visualization is selected by removing any accessory paths that run through small holes caused by anatomical variations or image segmentation artifacts.

The central path algorithm uses an object's three-dimensional skeleton to find a path that lies along the center of its lumen. First, a user picks a starting and an ending point for the path. These may be chosen using the multiplanar image display and a computer mouse. After the starting and ending points are selected, the algorithm performs a three-dimensional topological thinning of the object's region-grown segmented data. Thinning is like peeling an onion: the outer layers of the object are incrementally removed so that the overall topology (shape) is preserved. The resulting structure is a three-dimensional skeleton of the object, which, when the points are connected, generally consists of one-dimensional curves and two-dimensional surfaces. The thinning phase can be improved by using equivalence classes to classify neighborhoods of voxels instead of searching for all possible neighboring relationships.

This method of three-dimensional topological thinning is significant in three aspects. First, the determination of connectivity is more efficient because it is based on finding equivalence rather than searching all possible neighboring relationships, as is used in most conventional methods.

Second, the thinning process never examines background points more than once. Special data structures called queues are used to improve the efficiency of thinning. This method saves time compared to conventional methods by storing surface points (voxels on the outer surface of the region-grown object that are candidates for removal) in queues, after going through the original volume during a single pass. As thinning proceeds, newly exposed surface points are added to the queues whenever a surface point on the queue is removed. The thinning process stops when the queues become empty.

Third, the distance transform for the three-dimensional region-grown object is then calculated. The distance transform of a point in the object is the distance from this point to the nearest volume point not in the object. The distance transform is used to find the centers of maximally inscribed balls (CMB) in the object's lumen. A CMB can be thought of as the largest sphere that can fit into the lumen of the object. The centers of the CMB's can be used as anchor points in the thinning process, which insures that the generated central path is medially located and insensitive to the orientation of the original object (e.g., colon).

Many branches of medially located curves and surfaces will be generated in the thinning process, so the user defined starting and ending points are used to remove dead-end branches. The result is a curve that starts and ends at the specified points but may contain loops that represent accessory passages through the object that go to the same place.

The path selection phase converts the skeleton points into a graph representation by linking the points together into connected paths, which are called edges in the graph. The points where multiple paths meet are vertices in the graph. After the graph is built, unwanted edges are removed based on the radii of the CMB's associated with the points on the path, which is taken from the distance transform applied during the thinning phase.

The next step of path selection is basically a graph reduction process. A Greedy search algorithm is used for this purpose which removes all edges at each vertex except the two with the largest weights. The weight of each edge is a function of the radii of the points of the edge. One effective weighting method finds the smallest CMB radius of all points on the edge. Alternatively, the user may manually select the incorrect edges. After all incorrect edges have been removed, the remaining edges form the central path along the lumen of the object, such as the central path of the colon.

Alternatively, the central path can be determined by selecting a first seed point which lies within the lumen of the segmented object. The plane passing through that point that has the minimum area of object dissection is determined and the center of such area calculated. A new seed point is then selected which lies a pre-determined distance away from the first seed point in a perpendicular direction relative to the plane of minimum area passing through the first seed point. A plane of minimum area that passes through the new seed point is determined and the center calculated. This iterative process is continued until a central path connecting the center points is determined.

Figure 10A:
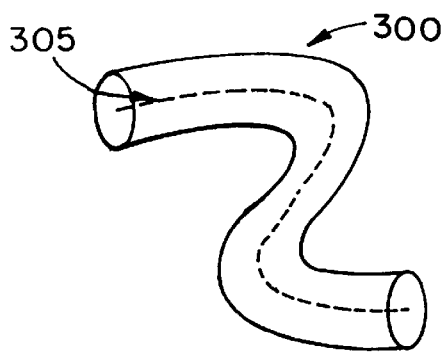
FIG. 10a–h are schematic illustrations depicting a process for splitting a colon.
Figure 10B:
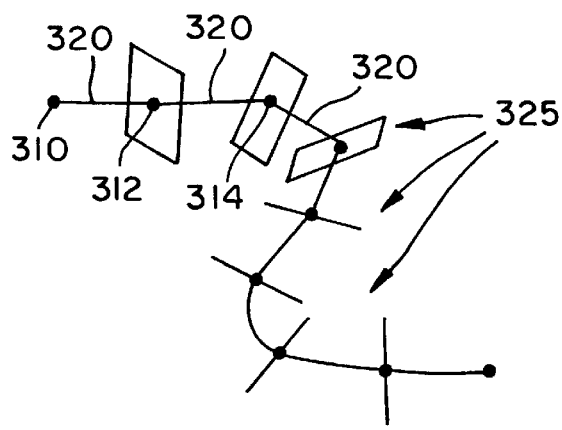
Figure 10C:
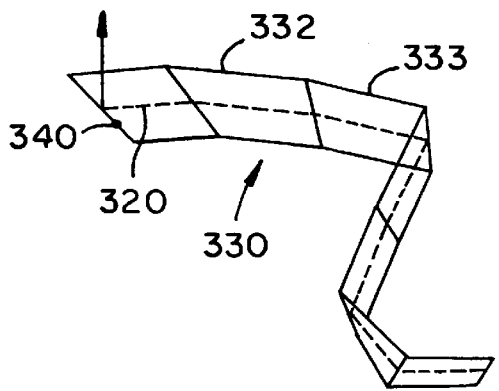
Figure 10D:
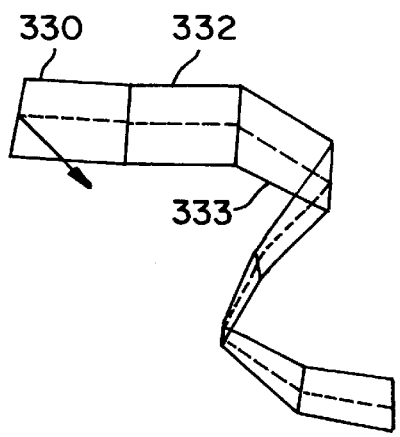

Referring to FIG. 10a, a segment of colon 300 is schematically depicted having a center line 305. Now returning to splitting the object, by variably subsampling points 310, 312, 314 along the central path, as shown in FIG. 10b, a sequence of consecutive points, connected by line segments 320, are determined. For each pair of these line segments connected at a point, a slicing plane 325 perpendicular to the line segment (a portion of the central path) and containing the point is calculated. For each of these line segments, a halving plane 330 is determined, as shown in FIG. 10c. The first halving plane is calculated to contain the line segment 320 and a point 340, arbitrarily specified by an angle offset from a predetermined axis perpendicular to the line segment. By changing the angle offset, as shown in FIG. 10d, the halving plane 330 is rotated around the line segment (like the hands of a clock). The second halving plane 332 is calculated to contain the second line segment and the intersection of the first halving plane with the first slicing plane. This second halving plane is unique and solely dependent on the orientation of the first halving plane. Accordingly, rotating the initial halving plane rotates the second halving plane. Similarly, the third halving plane 323 is calculated to contain the third line segment, and the intersection of the second halving plane with the second slicing plane, and so forth. The resulting connected halving planes approximate a curved cutting surface that follows the central path, and the resulting slicing planes are used in conjunction with the the re-ordered connectivity matrices to split along the halving planes.

Figure 10E:
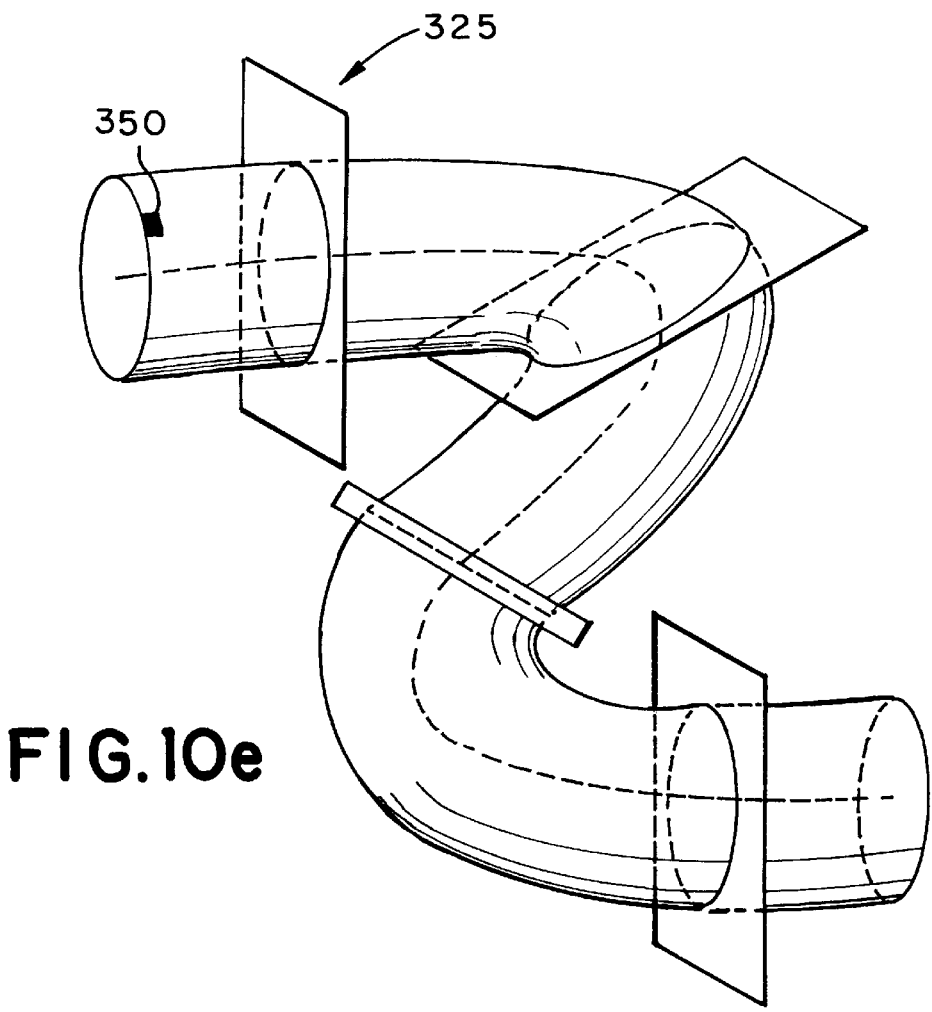
Figure 10F:
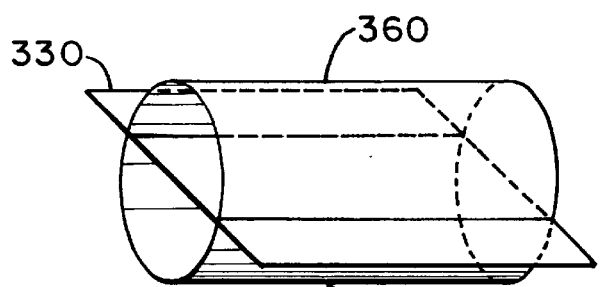
Figure 10G:
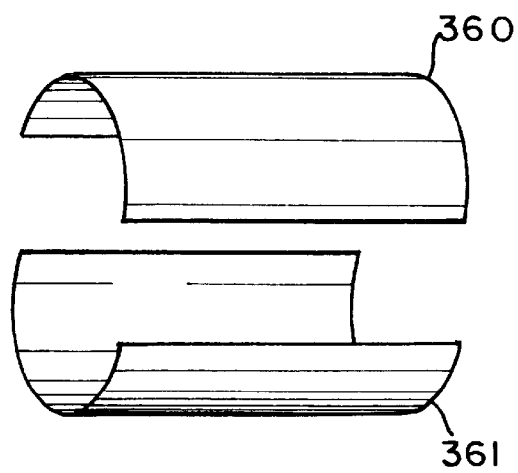
Figure 10H:
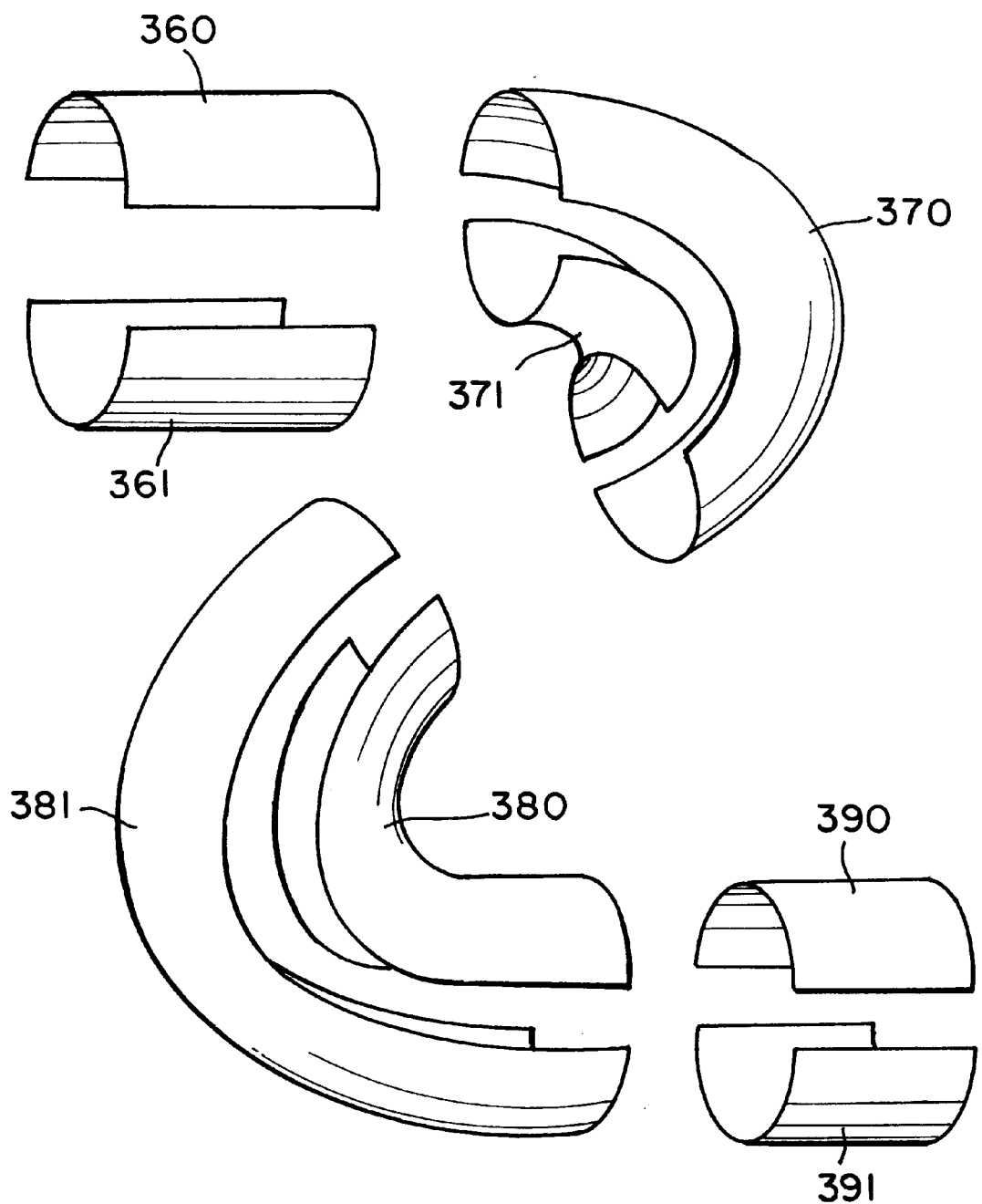

The splitting of the wireframe model is, then, accomplished, as shown in FIG. 10e, by selecting and marking an initial seed polygon 350. Using the re-ordered connectivity matrices, polygons adjacent to the seed are checked against the first slicing plane 325, marking those that are on the same side as the seed polygon. Each of the newly checked and marked polygons becomes a new seed, and each of its unchecked and unmarked polygons are identically checked against the first slicing plane until all polygons sequentially connected to the original seed polygon are marked. As shown in FIG. 10f, each of these marked polygons are then checked against the first halving plane 330 and stored, divided along the plane 330 to provide colon halves 360 and 361, as shown in FIG. 10g. An unmarked polygon adjacent to the last marked polygon is used as a seed for the second iteration of this process, as it is repeated until no unmarked and unchecked polygons remain. As shown ni FIG. 10h, the resulting split and halved segments 360 and 361, 370 and 371, 380 and 381, and 390 and 391, may be displayed individually or in groups, and can be color enhanced to easily identify interior and exterior surfaces.

In an alternate embodiment, the user is presented with a volume rendered display centered on the centroid of a selected abnormal population. For example, a volume-rendered view of a subvolume of user defined size centered on the centroid of the population can be displayed for visual inspection. Volume rendering is a visualization technique that creates a three-dimensional image using all of the volume data, rather than only an extracted surface representation. Traditionally, volume rendering is accomplished by projecting a series of rays from the user's viewpoint through the data volume. The color at each point (i.e., pixel) in the resulting three-dimensional image is determined by calculating a weighted sum of all voxels along each ray. This weighting factor is determined by a transfer function that is computed during a process called classification.

Altering the transfer function during volume rendering can reveal different characteristics of the rendered data and, thus, it is often desirable to interactively reclassify and re-render the data. However, the rate at which images are rendered can be slow for data volumes as large as the ones typically used in medical imaging. Accordingly, it can be beneficial to use texture mapping to dramatically increase the rate at which volume rendering is performed. In texture mapping, volume data is considered to be a series of two-dimensional textures that are interpolated, projected, and displayed rapidly on a series of polygons using specialized computer hardware.

The texture mapped volume rendering method uses high-speed texture memory and blending hardware available on a Silicon Graphics' computer workstation to approximate the results of the more computationally expensive ray-casting algorithm. The volume data is first loaded into texture memory. The textures are then semi-transparently mapped onto a series of parallel two-dimensional rectangles that correspond to slices of the volume. The texture mapped rectangles are then drawn and blended to allow the user to see through the volume. The colors and transparencies of the resulting three-dimensional object are controlled by color and opacity transfer functions. The entire volume can then be viewed by stacking the texture mapped rectangles in the proper order and looking toward the stack. Since viewing the stack along one of its edges does not optimally display the volume, a new stack is generated which is orthogonal to the original stack. This new stack is then used to display the volume along an edge. Likewise, for any additional viewing angles, additional stacks may be required. Generating the stacks is a dynamic process and each stack can be generated on an as needed basis. Texture mapping can use standard two-dimensional texture memory or faster three-dimensional texture memory.

In yet another alternate embodiment, upon selection of a population from the listing, the user can be presented with a three-dimensional, surface-rendered wireframe model of the population embedded within a volume-rendered display using texture memory techniques. Such a display is useful to show the three-dimensional relationships between the wireframe model and the volume data. Embedding a surface-rendered model inside a volume rendering can be accomplished using texture memory since both techniques use semi-transparent or opaque surfaces to generate their imagery. However, if the surface rendering is semi-transparent, care must be taken to ensure that all objects are blended in the proper order (typically, from back to front). All or part of the volume can be rendered. For example, to view a small structure using volume rendering, a subvolume of data surrounding that structure can be rendered, as opposed to displaying the entire volume of data. It should also be appreciated that the multiplanar views and volume rendering can be combined in a similar manner.

If the user wants to view the results of the various rendering techniques using separate display windows, the user can clone the display window 200 so that the two (or more) display windows share the same data. However, each display window could render using different techniques (i.e., multiplanar display, surface rendering, volume rendering). Accordingly, the user could open a single window with all three rendering techniques and then clone the window three times to view each technique separately. Changes made to the data in any one of the connected windows would be propagated to all the cloned windows. Camera orientations could be synchronized between the separate windows to lock the views together. Position tracking techniques could show the camera position of one viewer in another, so that the user could follow the path of a three-dimensional camera moving inside the structure in one display window from an external perspective using a cloned display window with another three-dimensional camera from an overhead position.

Figure 7:
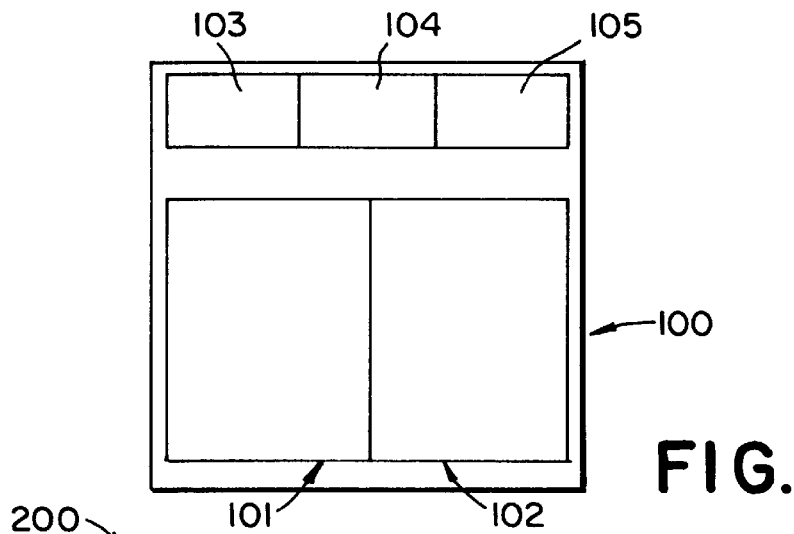
FIG. 7 is a schematic view of a display window for displaying a volume rendered image, a surface rendered image, and three multiplanar images along three different planes of a selected organ system.

An example of a computer console display 100 useful for displaying a three-dimensional rendering of a structure is shown in FIG. 7. The display 100 comprises a first window 101 for displaying a volume rendered image of the structure and a second window 102 for displaying a surface rendered image of the structure. Alternatively, the second window 102 can display a surface rendered image of the structure embedded within a volume rendered display, as described above. In addition, three multiplanar windows, 103, 104, and 105, are provided in a third window for displaying axial, coronal, sagittal, or oblique two-dimensional slices through the structure at a user-defined point, or at the centroid of a chosen population.

Figure 9:
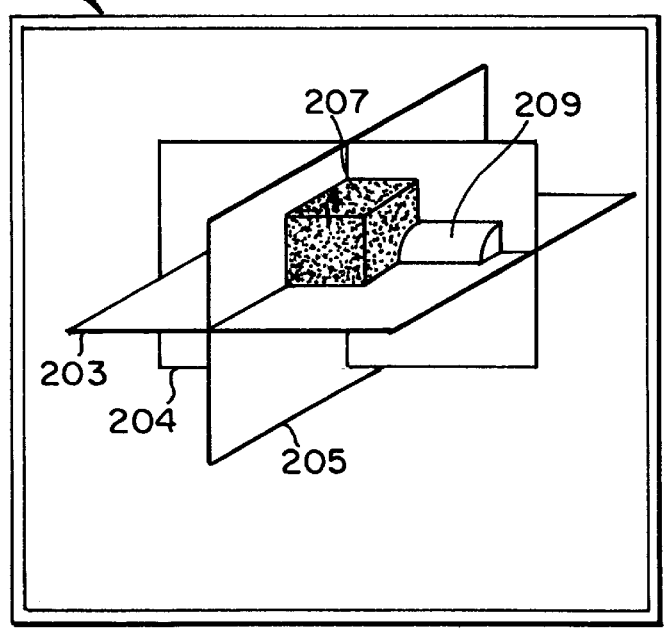
FIG. 9 is a schematic view of a display window for displaying a volume rendered image, a surface rendered image, and three multiplanar images along three different planes of a selected organ system combined in a single window display.

Alternatively a single window display 200, as shown in FIG. 9, can be used to display a three-dimensional rendering of the structure. The single window display comprises a single three-dimensional display window for presenting a combination of multiplanar images 203, 204 and 205 with a volume-rendered image 207 centered on a point located within a surface-rendered image 209. The display presents a holistic view of all the data that can aid in the visualization and understanding of the interrelationships of the various rendering techniques (i.e., surface rendering, volume rendering, and intersecting two-dimensional planes). The various rendering techniques can exist together because they are all based on the same patient coordinate system supplied by the image scanner, and they are all rendered using shared three-dimensional graphics techniques (texture memory) and a common graphics library. The intersecting planes can be rendered as opaque textures (as opposed to semi-transparent textures used in volume rendering) mapped onto two-dimensional rectangles using texture mapping and drawn in their proper orientation. The user can interactively scroll through slices parallel to any of the intersecting planes and can view any combination of planes (e.g., axial and/or sagittal and/or coronal planes), or the user can create and view an oblique slice plane. The planes can be rendered together with the surface data to show the exact relationship between the wireframe model and the volume (by viewing the intersections and orientations of the surface rendered wireframe model and the two-dimensional slices). They can be viewed together because the planes are rendered as any other kind of surface (i.e., a flat, two-dimensional rectangle).

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A computer-implemented method for interactively displaying a three-dimensional rendering of a structure having a lumen and indicating regions of abnormal wall thickness comprising the steps of:
   a. forming a three-dimensional volume of data from a series of two-dimensional images representing at least one physical property associated with the three-dimensional structure;
   b. creating an isosurface of a selected region of interest from the three-dimensional volume of data based on a selected value of the physical property representing the selected region of interest;
   c. generating a wireframe model of the isosurface, the wireframe model comprising a plurality of vertices;
   d. grouping the vertices of the wireframe model into populations having a characteristic indicating abnormal wall structure; and
   e. rendering the wireframe model in an interactive three-dimensional display to indicate the populations.

2. The method as recited in claim 1 wherein the step of grouping the vertices into populations comprises the steps of:
   a. determining a normal vector for each vertex position;
   b. determining a wall thickness value associated with each normal vector for each vertex;
   c. determining a connectivity matrix of contiguous vertices for each vertex; and
   d. grouping contiguous vertices having a characteristic indicating abnormal thicknesses into separate populations of abnormal thickness.

3. The method as recited in claim 2 wherein the step of determining the connectivity matrix comprises the step of re-ordering the connectivity matrix using local geometry connectivity information.

4. The method as recited in claim 1 further comprising the step of analyzing each population according to selected shape characteristics.

5. The method as recited in claim 4 wherein the step of analyzing each population according to shape characteristics comprises the step of determining a convexity value for each population representing an amount and direction of curvature.

6. The method as recited in claim 4 wherein the step of analyzing each population according to shape comprises the step of determining a curvature for each population.

7. A method for interactively displaying a three-dimensional rendering of a structure having a lumen comprising the steps of:
   a. forming a three-dimensional volume of data from a series of two-dimensional images representing at least one physical property associated with the three-dimensional structure;
   b. segmenting a selected region of interest from the three-dimensional volume of data based on a threshold value of the physical property, wherein the threshold value is adaptively adjusted in the region of interest;
   c. creating an isosurface of a selected region of interest from the three-dimensional volume of data based on selected values of the physical property representing the selected region of interest;
   d. generating a wireframe model of the isosurface; and
   e. rendering the wireframe model in an interactive three-dimensional display.

8. A system for interactively displaying a three-dimensional rendering of a structure having a lumen and indicating regions of abnormal wall thickness comprising:
   a. volume formation means for forming a three-dimensional volume of data from a series of two-dimensional images representing at least one physical property associated with the three-dimensional structure;
   b. isosurface creation means for creating an isosurface of a selected region of interest from the three-dimensional volume of data based on a selected value of the physical property representing the selected region of interest;
   c. wireframe generation means for generating a wireframe model of the isosurface, the wireframe model comprising a plurality of vertices;
   d. vertex grouping means for grouping the vertices of the wireframe model into populations having abnormal wall structure; and
   e. rendering means for rendering the wireframe model in an interactive three-dimensional display.

9. A system for interactively displaying a three-dimensional rendering of a structure having a lumen and indicating regions of abnormal wall thickness comprising:

a. formation means for forming a three-dimensional volume of data from a series of two-dimensional images representing at least one physical property associated with the three-dimensional structure;

b. segmentation means for segmenting a selected region of interest from the three-dimensional volume of data based on a threshold value of the physical property, wherein the threshold value is adaptively adjusted;

c. isosurface creation means for creating an isosurface of a selected region of interest from the three-dimensional volume of data based on selected values of the physical property representing the selected region of interest;

d. wireframe generation means for generating a wireframe model of the isosurface, the wireframe model comprising a plurality of vertices; and e. rendering means for rendering the wireframe model in an interactive three-dimensional display.

10. The method as recited in claim 1 wherein the rendering step comprises splitting the structure open in lengthwise sections and displaying the split open structure so that inner surfaces of the split open structure are visible.

11. The method as recited in claim 7 wherein the rendering step comprises splitting the structure open in lengthwise sections and displaying the split open structure so that inner surfaces of the split open structure are visible.

12. The system as recited in claim 8 wherein the rendering means comprises means for splitting the structure open in lengthwise sections and displaying the split open structure so that inner surfaces of the split open structure are visible.

13. The system as recited in claim 9 wherein the rendering means comprises means for splitting the structure open in lengthwise sections and displaying the split open structure so that inner surfaces of the split open structure are visible.

14. The method as recited in claim 1 wherein the rendering step comprises simulating movement along a line which passes along the center of the lumen of the structure.

15. The method as recited in claim 7 wherein the rendering step comprises simulating movement along a line which passes along the center of the lumen of the structure.

16. The system as recited in claim 8 wherein the rendering means comprises means for simulating movement along a line which passes along the center of the lumen of the structure.

17. The system as recited in claim 9 wherein the rendering means comprises means for simulating movement along a line which passes along the center of the lumen of the structure.

18. The method as recited in claim 1 comprising the step of displaying a volume-rendered image of the interactive three-dimensional display centered on a point located within a surface-rendered image of the interactive three-dimensional display.

19. The method as recited in claim 18 wherein the step of displaying the interactive three-dimensional display comprises the step of displaying at least one planar image through a second point located within the surface-rendered image of the interactive three-dimensional display.

20. The method as recited in claim 7 comprising the step of displaying a volume-rendered image of the interactive three-dimensional display centered on a point located within a surface-rendered image of the interactive three-dimensional display.

21. The method as recited in claim 20 wherein the step of displaying the interactive three-dimensional display comprises the step of displaying at least one planar image through a second point located within the surface-rendered image of the interactive three-dimensional display.

22. The system as recited in claim 8 comprising means for displaying a volume-rendered image of the interactive three-dimensional display centered on a point located within a surface-rendered image of the interactive three-dimensional display.

23. The system as recited in claim 22 wherein the display means comprises means for displaying at least one planar image through a second point located within the surface-rendered image of the interactive three-dimensional display.

24. The system as recited in claim 9 comprising means for displaying a volume-rendered image of the interactive three-dimensional display centered on a point located within a surface-rendered image of the interactive three-dimensional display.

25. The system as recited in claim 24 wherein the display means comprises means for displaying at least one planar image through a second point located within the surface-rendered image of the interactive three-dimensional display.

26. A method for interactively displaying three dimensional structures comprising the steps of:

a. forming a three-dimensional volume of data from a series of two-dimensional images representing at least one physical property associated with a three dimensional body;

b. segmenting a selected region of interest from the volume of data based on selected values of the physical property representing the selected region of interest;

c. rendering the segmented region of interest as a surface rendered image in an interactive three-dimensional display, therein producing a virtual three-dimensional environment; and d. displaying a volume-rendered image of the interactive three-dimensional display adjoining the surface-rendered image.

27. The method as recited in claim 26 wherein the step of displaying the interactive three-dimensional display comprises the step of displaying at least one planar image through the surface-rendered image of the interactive three-dimensional display.

28. A method for interactively displaying three dimensional structures comprising the steps of:

a. forming a three-dimensional volume of data from a series of two-dimensional images representing at least one physical property associated with a three dimensional body;

b. segmenting a selected region of interest from the volume of data based on selected values of the physical property representing the selected region of interest;

c. determining an arbitrarily oriented cross-sectional area of the selected region of interest; and d. rendering the segmented region of interest in an interactive three-dimensional display, therein producing a virtual three-dimensional environment.

29. A method for interactively displaying three dimensional structures comprising the steps of:

a. forming a three-dimensional volume of data from a series of two-dimensional images representing at least one physical property associated with a three dimensional body;

b. segmenting a selected region of interest from the volume of data based on selected values of the physical property representing the selected region of interest;

c. generating a wireframe model of the segmented region of interest, wherein the wireframe model comprises a plurality of vertices and information regarding the connectivity of the plurality of vertices is provided by connectivity matrices;

d. re-ordering the connectivity matrices; and e. rendering the segmented region of interest in an interactive three-dimensional display, therein producing a virtual three-dimensional environment.

30. The method as recited in claim 29 comprising the step of determining an arbitrarily oriented cross-sectional area of the selected region of interest.

31. A method for indicating regions of a three-dimensional structure having an abnormal wall characteristic comprising:

a. forming a three-dimensional volume of data representing at least one physical property associated with the three-dimensional structure, the three-dimensional volume of data comprising a three-dimensional matrix of voxels wherein each voxel has an associated voxel value; and b. grouping the voxels, as a selected function of voxel value, into populations having a characteristic indicating abnormal wall structure.

32. The method as recited in claim 31 wherein the step of grouping the voxels into populations comprises the step of grouping contiguous voxels having a characteristic indicating abnormal wall thickness into separate populations of abnormal thickness.

33. A method for interactively displaying a three-dimensional rendering of a three-dimensional structure having a lumen comprising the steps of:

a. forming a three-dimensional volume of data representing at least one physical property associated with the three-dimensional structure;

b. segmenting a selected region of interest from the three-dimensional volume of data;

c. creating a surface of the selected region of interest based on selected values of the physical property representing the selected region of interest; and d. grouping regions of the surface into populations having a characteristic indicating abnormal structure.

34. The method as recited in claim 33 wherein the step of grouping regions of the isosurface into populations comprises the step of grouping contiguous regions of the isosurface having a characteristic indicating abnormal thicknesses into separate populations of abnormal thickness.

35. A method for indicating regions of a three-dimensional structure having an abnormal wall characteristic comprising:

a. forming a three-dimensional volume of data representing at least one physical property associated with the three-dimensional structure;

b. constructing a three-dimensional model of the three-dimensional structure from the three-dimensional volume of data; and c. grouping regions of the three-dimensional model into populations having a characteristic indicating abnormal structure.

36. The method as recited in claim 35 wherein the step of grouping regions of the three-dimensional model into populations comprises the step of grouping contiguous regions of the three-dimensional model having a characteristic indicating abnormal thicknesses into separate populations of abnormal thickness.

37. A system for indicating regions of a three-dimensional structure having an abnormal wall characteristic comprising:

a. volume formation means for forming a three-dimensional volume of data representing at least one physical property associated with the three-dimensional structure, the three-dimensional volume of data comprising a three-dimensional matrix of voxels wherein each voxel has an associated voxel value; and b. voxel grouping means for grouping the voxels, as a selected function of voxel value, into populations having a characteristic indicating abnormal wall structure.

38. The system as recited in claim 37 wherein the voxel grouping means comprises means for grouping contiguous voxels having a characteristic indicating abnormal wall thickness into separate populations of abnormal thickness.

39. A system for interactively displaying a three-dimensional rendering of a three-dimensional structure having a lumen comprising:

a. formation means for forming a three-dimensional volume of data representing at least one physical property associated with the three-dimensional structure;

b. segmentation means for segmenting a selected region of interest from the three-dimensional volume of data;

c. surface creation means for creating a surface of the selected region of interest based on selected values of the physical property representing the selected region of interest; and d. surface grouping means for grouping regions of the surface into populations having a characteristic indicating abnormal wall structure.

40. The system as recited in claim 39 wherein the surface grouping means comprises means for grouping contiguous regions of the surface having a characteristic indicating abnormal thicknesses into separate populations of abnormal thickness.

41. A system for indicating regions of a three-dimensional structure having an abnormal wall characteristic comprising:

a. formation means for forming a three-dimensional volume of data representing at least one physical property associated with the three-dimensional structure;

b. modeling means for constructing a three-dimensional model of the three-dimensional structure from the three-dimensional volume of data; and c. grouping means for grouping regions of the three-dimensional model into populations having a characteristic indicating abnormal structure.

42. The system as recited in claim 41 wherein the grouping means comprises means for grouping contiguous regions of the three-dimensional model having a characteristic indicating abnormal thicknesses into separate populations of abnormal thickness.

43. A method for indicating regions of a colon having an abnormal wall characteristic comprising:

b. inflating the colon with gas;

c. forming a three-dimensional volume of data representing at least one physical property associated with the colon, the three-dimensional volume of data comprising a three-dimensional matrix of voxels wherein each voxel has an associated voxel value; and d. grouping the voxels, as a selected function of voxel value, into populations having a characteristic indicating abnormal wall structure.

44. A system for indicating regions of a colon having an abnormal wall characteristic comprising:

a. colon preparation means for inflating the colon with gas;

b. volume formation means for forming a three-dimensional volume of data representing at least one physical property associated with the colon, the three-dimensional volume of data comprising a three-dimensional matrix of voxels wherein each voxel has an associated voxel value; and c. voxel grouping means for grouping the voxels, as a selected function of voxel value, into populations having a characteristic indicating abnormal wall structure.

45. The method as recited in claims 31, 33, or 35 further comprising the step of analyzing each population according to selected shape characteristics.

46. The method as recited in claim 45 wherein the step of analyzing each population according to shape characteristics comprises the step of determining a convexity value for each population representing an amount and direction of curvature.

47. The method as recited in claim 45 wherein the step of analyzing each population according to shape characteristics comprises the step of determining a curvature for each population.

48. The system as recited in claims 37, 39, or 41 further comprising a population analyzing means for analyzing each population according to selected shape characteristics.

49. The system as recited in claim 48 wherein the population analyzing means comprises means for determining a convexity value for each population representing an amount and direction of curvature.

50. The system as recited in claim 48 wherein the population analyzing means comprises means for determining a curvature for each population.

* * * * *